United States Patent
Sohn

(10) Patent No.: US 7,128,575 B1
(45) Date of Patent: Oct. 31, 2006

(54) TOOTH ELEVATOR

(76) Inventor: Jung W. Sohn, 600 W. 9th St., #904, Los Angeles, CA (US) 90015

( * ) Notice: Subject to any disclaimer, the term of this patent is extended or adjusted under 35 U.S.C. 154(b) by 225 days.

(21) Appl. No.: 10/228,609

(22) Filed: Aug. 26, 2002

(51) Int. Cl.
*A61C 3/14* (2006.01)
*B25B 7/02* (2006.01)

(52) U.S. Cl. .................. 433/159; 81/418; 81/426.5

(58) Field of Classification Search .......... 433/159, 433/160, 4; 81/300, 418, 424.5, 426, 426.5
See application file for complete search history.

(56) References Cited

U.S. PATENT DOCUMENTS

| | | | |
|---|---|---|---|
| 75,716 A | 3/1868 | Woolverton | 433/159 |
| 491,932 A | 2/1893 | Whitlock | 433/159 |
| 1,376,005 A | 4/1921 | Cohane | 433/146 |
| 1,395,714 A | 11/1921 | Johnson | 433/159 |
| 1,507,738 A | 9/1924 | Johnson | 433/159 |
| 1,626,226 A * | 4/1927 | Cantor | 433/159 |
| 1,636,861 A | 7/1927 | Griveau | 433/159 |
| 1,675,815 A | 7/1928 | Miller | 433/159 |
| 1,730,230 A | 10/1929 | Miller | 433/159 |
| 1,762,888 A | 6/1930 | Roberts | 433/159 |
| 2,030,798 A | 2/1936 | Krajeski | 433/159 |
| 2,497,254 A | 2/1950 | Brantley | 433/146 |
| 2,632,248 A | 3/1954 | Köhler | 433/160 |
| 2,944,341 A | 7/1960 | Lane | 433/159 |
| 4,031,624 A | 6/1977 | Heimann | 433/159 |
| 5,421,721 A * | 6/1995 | Fyffe | 433/159 |
| 6,042,379 A | 3/2000 | Rodriguez del Val | 433/159 |
| 6,210,161 B1 | 4/2001 | Montgomery | 433/146 |
| 6,394,805 B1 * | 5/2002 | Rabal | 433/159 |

* cited by examiner

*Primary Examiner*—John J Wilson
(74) *Attorney, Agent, or Firm*—David A. Belasco; Belasco Jacobs & Townsley, LLP

(57) ABSTRACT

A tooth elevator designed to minimize risk of injury to a patient's mouth or adjacent teeth during tooth extraction is described. The elevator has mating side members, a handle portion and a mating jaw portion. As force is applied to the handle portions, the jaw portions are urged together on either side of a molar to be extracted. Inward curving side members disjoint the tooth upwardly while an angled front face simultaneously moves the tooth back, loosening it for extraction. A variation of the tooth elevator has a downward angled offset that allows a practitioner to easily position the elevator in a patient's mouth without the discomfort of raising the elbow of the grasping hand. The handle portions may also have non-slip features.

6 Claims, 3 Drawing Sheets

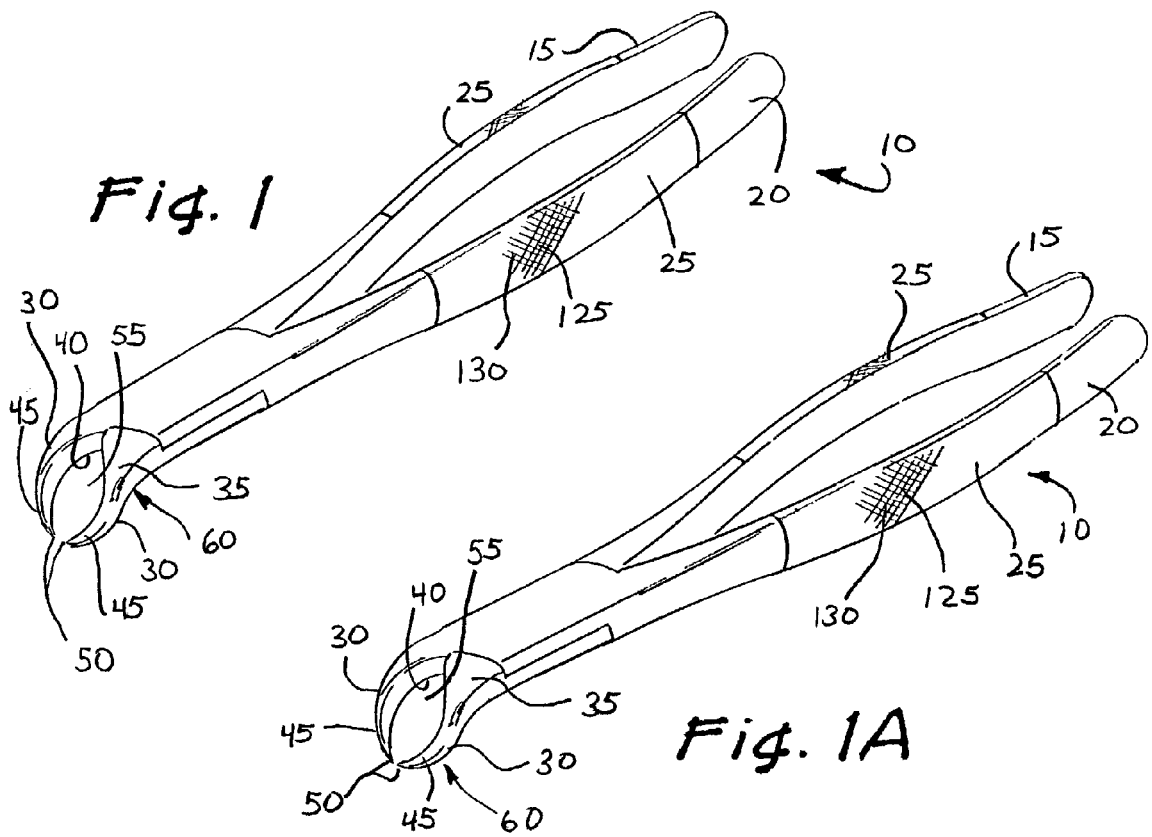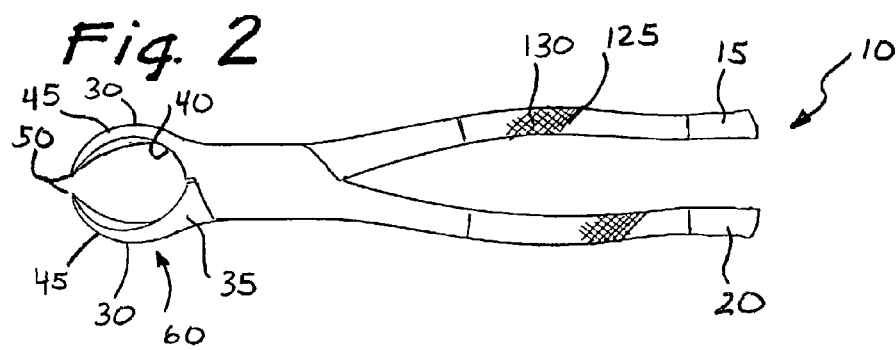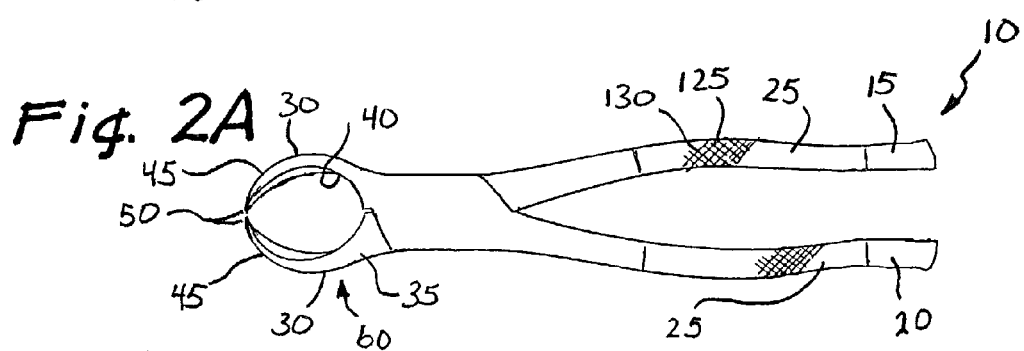

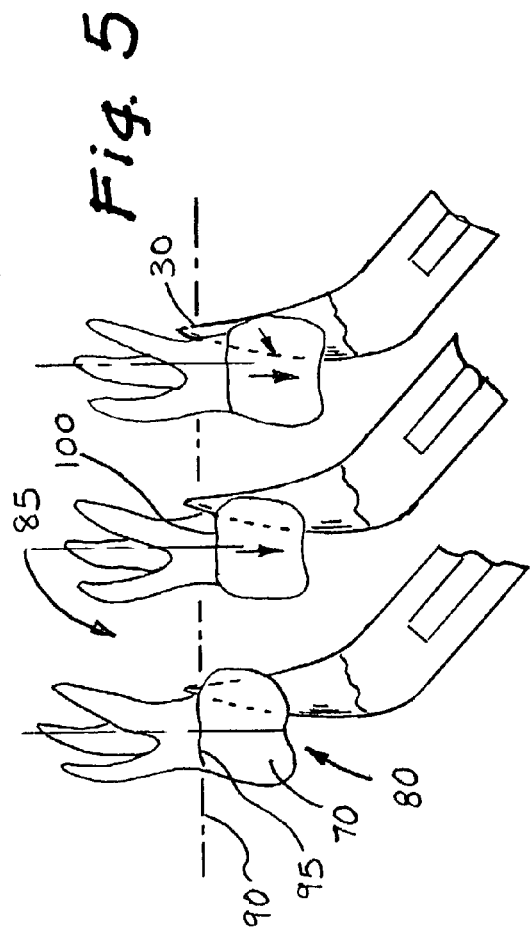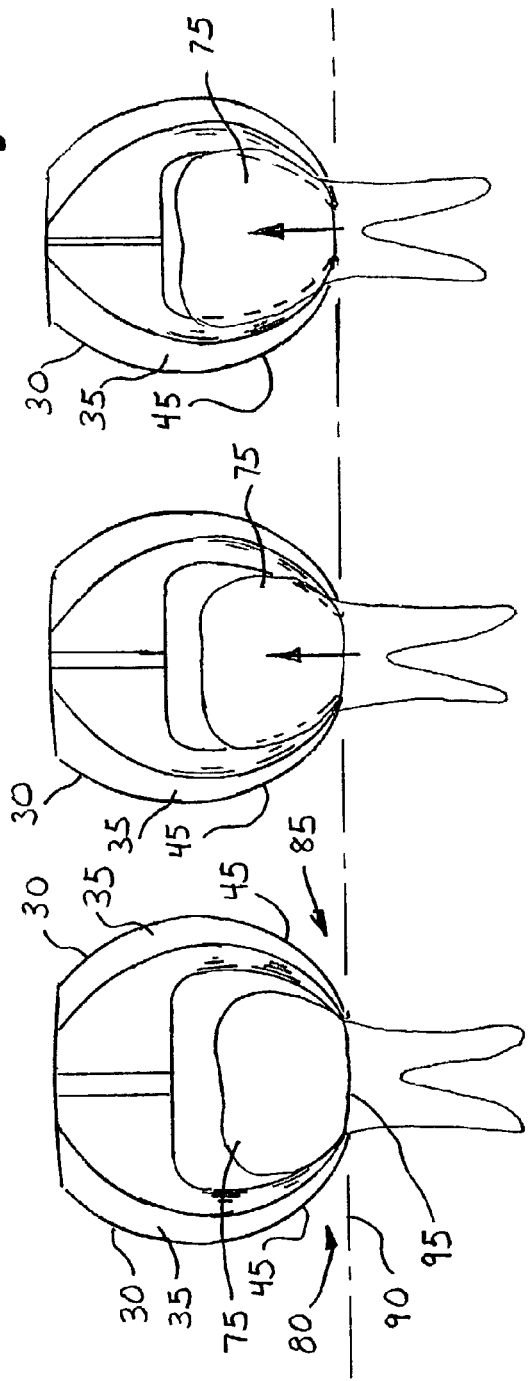

TOOTH ELEVATOR

FIELD OF INVENTION

The invention pertains to dental tools. More particularly, the invention relates to the tooth elevators designed to minimize the risk of injury to a patient or damage to adjacent teeth when removing a tooth.

BACKGROUND OF THE INVENTION

Various tools and devices have been developed for elevating teeth during the extraction process. The most common device used for this purpose is the straight elevator. This tool consists of a handle, a straight shaft and a rounded, scoop shaped tip. The elevator is placed perpendicular to the long axis of the alveolar ridge on the mesial aspect of the tooth, with the rounded side of its tip resting on the bone. The elevator is rotated away from the tooth, creating a "scooping" action to elevate the tooth. The elevator may also be rotated toward the tooth to luxate and move it posteriorly. The straight elevator can be problematic as it is difficult to control the force applied to such a tool. If the practitioner slips while attempting to elevate a tooth, it is possible to penetrate the cheek of the patient or damage adjacent teeth. In difficult extractions, practitioners are often tempted to use the straight elevator as a lever against adjacent teeth. This practice can result in broken teeth and related complications.

U.S. Pat. No. 6,042,379 issued to Rodriguez del Val is directed to a dental raising forceps for the rearmost upper molars or their remains. The reference describes a bayonet forceps with pointed jaws that are somewhat half-moon in shape with rounded points used to loosen and elevate the last molar or remains of the root thereof. The forceps comprise a handle portion, a hinge and symmetrically curved jaws. The points of the jaws are inserted between the second and third upper molars, which loosens and raises the molar or the remains of the roots. Conventional forceps are then used to complete the extraction. This invention is useful only for rearmost upper molars and only to luxate the tooth posteriorly as its jaws have only a single working surface. Further, the Rodriguez del Val forceps uses an adjacent tooth as a fulcrum, inviting the possibility of damaging the adjacent tooth.

U.S. Pat. No. 1,507,738 issued to Johnson, discloses elevating forceps that are used to operate on the third lower molar in order to facilitate the removal thereof. The forceps shown in this reference comprise handles which are pivotally connected by a pin with jaws or beaks that are made with a slight off-set so that when the device is closed the tips will pass or overlap one another. The cross-section of the jaws is wedge-shaped and this construction serves to effect a wedging on the tooth to be extracted. Beaks also have a bend in the forward direction that results in further displacement of the tooth as the jaws of the forceps are closed.

U.S. Pat. No. 6,210,161, issued to Montgomery is directed to a breakdown dental forceps. The forceps seen in this patent have tapered jaws with concave inner surfaces that allow the forceps to be used to grasp the mesial and distal surfaces of a molar, thus providing more gripping area and easier extraction. The jaw point is employed to loosen an individual section of root by placing the jaw point against the outside surface of the root and applying rotational force which causes the root to be loosened and therefore easier to remove. This invention provides for a narrow set of jaws for grasping a tooth in narrow confines. In addition, it is designed to provide the ability to twist a tooth in order to loosen it.

While other variations exist, the above described designs for tooth elevators and forceps are typical of those encountered in the prior art. It is an objective of the present invention to provide a safe and effective means for elevating upper and lower posterior teeth prior to extraction. It is a further objective to provide such elevation while minimizing the chance of causing complications and damage to surrounding tissues. It is a still further objective of the invention to provide a tooth elevator in which the amount of force applied can be easily controlled and for which accessibility is improved when compared with conventional elevators. It is yet a further objective to provide a tooth elevator that can be safely used for sectioning a tooth after a slot has been made with a rotary drill at the point where the tooth is to be split. Finally, it is an objective of the invention to provide a tooth elevator that is easily used by practitioners who are unable to apply a great deal of force to a conventional elevator.

While some of the objectives of the present invention are disclosed in the prior art, none of the inventions found include all of the requirements identified.

SUMMARY OF THE INVENTION

The present invention addresses all of the deficiencies of prior art tooth elevating inventions and satisfies all of the objectives as described above.

A tooth elevator providing the desired features may be constructed from the following components. First and second mating side members are provided. Each of the side members has a handle portion and a mating jaw portion. The jaw portion extends forwardly from the handle portion. The first side member is hingedly attached to the second side member between the jaw portion and the handle portion.

Each of the mating jaw portions is wedge shaped in cross-section and have an angled front face, a rear face, and inward curving side members tapering to a point. The mating jaw portions form an elongated ovoid shape when in a closed position.

The mating jaw portions are inserted into a sulcus of either of an upper or lower molar from buccal and opposite sides. As force is applied to the handle portions, the mating jaw portions are urged together between an alveolar bone and a coronal portion of the molar adjacent a cemento-enamel junction. The inward curving side members luxate the molar vertically while the angled front face simultaneously moves the molar posteriorly, loosening the molar for extraction.

In one variant of the invention, the mating jaw portions include a downward angled offset. The offset allows a practitioner to more easily position the tooth elevator in a patient's mouth without uncomfortably raising an elbow of a hand grasping the handle portions.

In another variant, the rear face is planar, and the angled front face and the planar rear face form an acute angle ranging between 35 and 70 degrees.

In still another variant, the downward angled offset ranges from 30 to 60 degrees to a plane parallel to a length of the first and second mating side members.

In yet another variant, the handle portions include non-slip features.

In still a further variant, the non-slip features are selected from the group including knurling, serrating, stippling, rubber coating and silicon coating.

In a final variant of the invention, the elevator is formed from material selected from the group including forged steel and forged stainless steel.

DESCRIPTION OF THE DRAWINGS

FIG. 1 is a perspective view of the preferred embodiment of the invention illustrating the handle portions, jaw portions spaced apart in the closed position and downward angled offset thereof;

FIG. 1A is a perspective view of an alternative embodiment of the invention illustrating the handle portions, jaw portions nearly touching in the closed position and downward angled offset thereof;

FIG. 2 is a plan view of the FIG. 1 embodiment;

FIG. 2A is a plan view of the FIG. 1A embodiment;

FIG. 5 is a side elevational detail view of the jaw portions of the FIG. 1 embodiment, illustrating the progressive elevation and reward luxation of a tooth; and FIG. 6 is a front elevational detail view of the jaw portions of the FIG. 1 embodiment, illustrating the elevation of a tooth.

DETAILED DESCRIPTION OF THE PREFERRED EMBODIMENT

Figure 3:
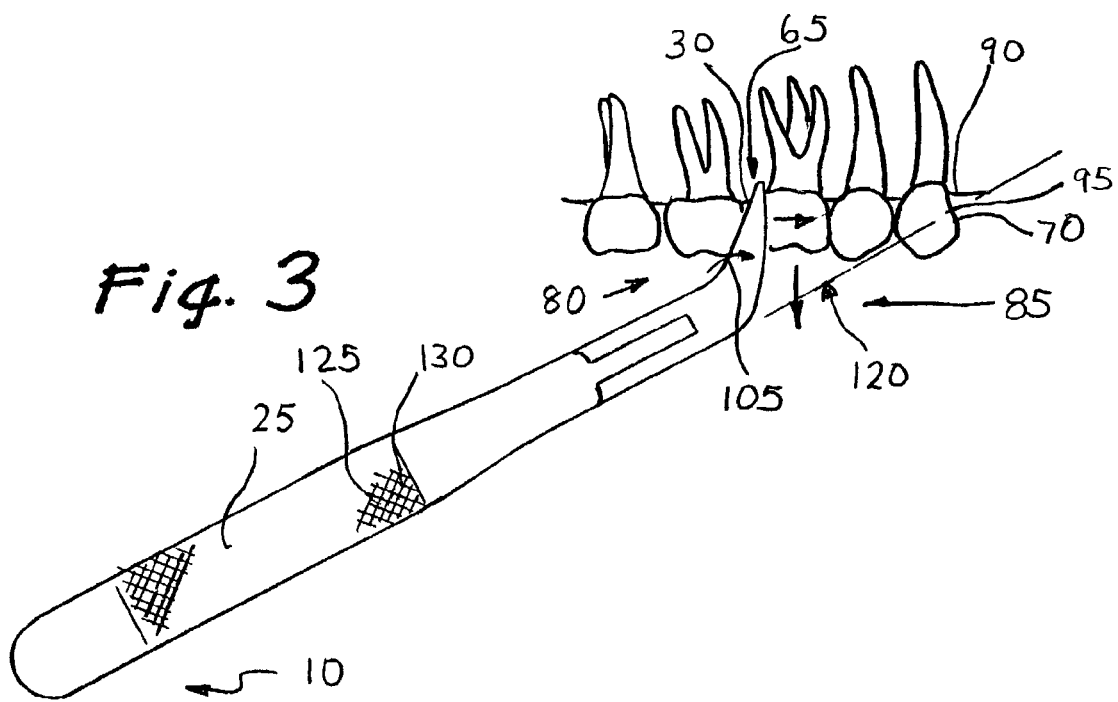
FIG. 3 is a side elevation of the FIG. 1 embodiment positioned to elevate an upper tooth.

FIGS. 1–6 illustrate a tooth elevator 10 which may be constructed from the following components. First 15 and second 20 mating side members are provided. Each of the side members 15, 20 has a handle portion 25 and a mating jaw portion 30. The jaw portion 30 extends forwardly from the handle portion 25. The first side member 15 is hingedly attached to the second side member 20 between the jaw portion 30 and the handle portion 25.

Each of the mating jaw portions 30 are wedge shaped in cross-section and have an angled front face 35, a rear face 40, and inward curving side members 45 tapering to a point 50. The mating jaw portions 30 form an elongated ovoid shape 55 when in a closed position 60.

The mating jaw portions 30 are inserted into a sulcus 65 of either of an upper 70 or lower 75 molar from buccal 80 and opposite 85 sides, as illustrated in FIGS. 3, 4, 5 and 6.

As force is applied to the handle portions 25, the mating jaw portions 30 are urged together between an alveolar bone 90 and a coronal portion 95 of the molar 70, 75 adjacent a cemento-enamel junction 100. The inward curving side members 45 luxate the molar 70, 75 vertically while the angled front face 35 simultaneously moves the molar 70, 75 posteriorly, loosening the molar 70, 75 for extraction.

In a variant of the invention, illustrated in FIG. 3, the mating jaw portions 30 include a downward angled offset 105. The offset 105 allows a practitioner to more easily position the tooth elevator 10 in a patient's mouth without uncomfortably raising an elbow of a hand (not shown) grasping the handle portions 25.

Figure 4:
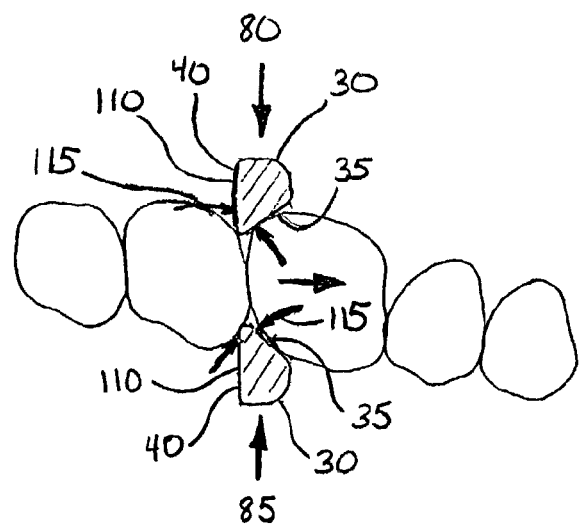
FIG. 4 is a cross-sectional plan view of the jaw portions of the FIG. 1 embodiment illustrating the rearward luxation of a tooth.

In another variant, as illustrated in FIG. 4, the rear face 40 is planar, and the angled front face 35 and the planar rear face 110 form an acute angle 115 ranging between 35 and 70 degrees.

In still another variant, illustrated in FIG. 3, the downward angled offset 105 ranges from 30 to 60 degrees to a plane 120 parallel to a length of the first 15 and second 20 mating side members.

In yet another variant, illustrated in FIGS. 1, 1A, 2, 2A and 3, the handle portions 25 include non-slip features 125.

In yet another embodiment, illustrated in FIGS. 1, 1A, 2, 2A and 3, the non-slip features 125 are selected from the group including knurling 130, serrating (not shown), stippling (not shown), rubber coating (not shown) and silicon coating (not shown).

In a final variant of the invention, the elevator 10 is formed from material selected from the group including forged steel and forged stainless steel.

The invention claimed is:

1. A tooth elevator, comprising:
   first and second mating side members, each of said side members having a handle portion and a mating jaw portion;
   said jaw portion extending forwardly from said handle portion;
   said first side member being hingedly attached to said second side member between said jaw portion and said handle portion;
   each of said mating jaw portions being wedge shaped in cross-section and having an angled front face, a rear face, and inward curving side members tapering to a point;
   said mating jaw portions forming an elongated ovoid shape when disposed in a closed position; and
   wherein said rear face is planar and said angled front face and said planar rear face include an acute angle ranging between 35 and 70 degrees.

2. A tooth elevator as described in claim 1, wherein said mating jaw portions further comprise a downward angled offset, said offset allowing a practitioner to more easily position the tooth elevator in a patient's mouth without uncomfortably raising an elbow of a hand grasping said handle portions.

3. A tooth elevator as described in claim 2, wherein said downward angled offset ranges from 30 to 60 degrees to a plane parallel to a length of said first and second mating side members.

4. A tooth elevator as described in claim 1, wherein said handle portions further comprise non-slip features.

5. A tooth elevator as described in claim 4, wherein said non-slip features are selected from the group comprising:
   knurling, serrating, stippling, rubber coating and silicon coating.

6. A tooth elevator as described in claim 1, wherein the elevator is formed from material selected from the group comprising:
   forged steel and forged stainless steel.

* * * * *